United States Patent
Coulombe

(10) Patent No.: US 11,806,063 B2
(45) Date of Patent: Nov. 7, 2023

(54) CRYOADHESIVE DEVICE FOR LEFT ATRIAL APPENDAGE OCCLUSION

(71) Applicant: Medtronic CryoCath LP, Toronto (CA)

(72) Inventor: Nicolas Coulombe, Anjou (CA)

(73) Assignee: Medtronic CryoCath LP, Toronto (CA)

( * ) Notice: Subject to any disclaimer, the term of this patent is extended or adjusted under 35 U.S.C. 154(b) by 1030 days.

(21) Appl. No.: 16/451,922

(22) Filed: Jun. 25, 2019

(65) Prior Publication Data

US 2019/0336195 A1    Nov. 7, 2019

Related U.S. Application Data

(62) Division of application No. 14/477,071, filed on Sep. 4, 2014, now Pat. No. 10,398,488.

(51) Int. Cl.
*A61B 18/02* (2006.01)
*A61B 17/00* (2006.01)
*A61B 18/00* (2006.01)

(52) U.S. Cl.
CPC .... *A61B 18/02* (2013.01); *A61B 2017/00358* (2013.01); *A61B 2018/00232* (2013.01);
(Continued)

(58) Field of Classification Search
CPC .......... A61B 18/02; A61B 2018/00232; A61B 2018/00363; A61B 2018/0212;
(Continued)

(56) References Cited

U.S. PATENT DOCUMENTS 6,066,132 A * 5/2000 Chen .................. A61B 18/08
607/113
6,270,493 B1   8/2001 Lalonde et al.
(Continued)

FOREIGN PATENT DOCUMENTS

CN          1269708 A    11/2000
CN        103200889 A     7/2013
(Continued)

OTHER PUBLICATIONS

Wolf, Philip A., Atrial Fibrillation as an Independent Risk Factor for Stroke: The Framingham Study. Stroke, Journal of the American Heart Association, 1991;22:983-988, Dallas Texas.
(Continued)

*Primary Examiner* — Daniel W Fowler
(74) *Attorney, Agent, or Firm* — Michael Best & Friedrich LLP

(57) ABSTRACT

An epicardial device, system, and method for stabilizing the left atrial appendage during a left atrial appendage ligation/occlusion procedure. A cryoadhesion device including a stabilization element is positioned within the pericardial space proximate the left atrial appendage through subxiphoid access. Once the stabilization element is in contact with the left atrial appendage, the stabilization element is cooled to a temperature that is sufficient to cryoadhere the stabilization element to the left atrial appendage. In this way, the cryoadhesion device stabilizes the left atrial appendage in order to perform left atrial appendage ligation/occlusion with a secondary medical device.

12 Claims, 12 Drawing Sheets

(52) U.S. Cl.
CPC ............... *A61B 2018/00363* (2013.01); *A61B 2018/0212* (2013.01); *A61B 2018/0237* (2013.01); *A61B 2018/0262* (2013.01); *A61B 2018/0293* (2013.01)

(58) Field of Classification Search
CPC .... A61B 2018/0237; A61B 2018/0262; A61B 2018/0293
See application file for complete search history.

(56) References Cited

U.S. PATENT DOCUMENTS

| | | | |
|---|---|---|---|
| 7,582,083 | B2 | 9/2009 | Swanson |
| 8,409,216 | B2 | 4/2013 | Parihar et al. |
| 2003/0060685 | A1 | 3/2003 | Houser et al. |
| 2004/0199154 | A1 | 10/2004 | Nahon et al. |
| 2006/0020271 | A1 | 1/2006 | Stewart et al. |
| 2007/0083225 | A1 | 4/2007 | Kiser et al. |
| 2008/0243111 | A1 | 10/2008 | Gammie et al. |
| 2011/0112569 | A1 | 5/2011 | Friedman et al. |
| 2011/0276075 | A1 | 11/2011 | Fung et al. |
| 2012/0035584 | A1 | 2/2012 | Thompson-Nauman et al. |
| 2012/0101485 | A1 | 4/2012 | Wittenberger |
| 2012/0108953 | A1* | 5/2012 | Markowitz ............ A61B 18/02 606/21 |
| 2012/0109116 | A1* | 5/2012 | Asconeguy ............ A61B 18/02 606/21 |
| 2012/0143179 | A1 | 6/2012 | Avitall |
| 2014/0081111 | A1 | 3/2014 | Tun et al. |

FOREIGN PATENT DOCUMENTS

| | | |
|---|---|---|
| EP | 1430848 A1 | 6/2004 |
| EP | 2019633 B1 | 8/2012 |
| EP | 2482735 A2 | 8/2012 |
| WO | 00/48672 A1 | 8/2000 |
| WO | 2012051697 A1 | 4/2012 |
| WO | 2014031903 A1 | 2/2014 |

OTHER PUBLICATIONS

Jastrzebski, Marek, Md, PhD, et al.. Cryocatheter as a tool for retrieving endovascular foreign bodies. Heart Rhythm 2013;10:1357-1358. http://dx.doi.org/10.1016/j.hrthm.2012.05.027.

International Search Report and Written Opinion dated Nov. 3, 2015, for corresponding International Application No. PCT/CA2015/050834; International Filing Date: Aug. 31, 2015 consisting of 13-pages.

Johansson, B. et al., Atrial function after left atrial epicardial cryoablation for atrial fibrillation in patients undergoing mitral valve surgery. Journal of Interventional Cardiac Electrophysiology, vol. 33, Issue 1, Jan. 2012, pp. 85-91.

Carina Blomstrom-Lundqvist et al., A randomized double-blind study of epicardial left atrial cryoablation for permanent atrial fibrillation in patients undergoing mitral valve surgery: the SWEDish Multicentre Atrial Fibrillation study (SWEDMAF), European Heart Journal, (2007) 28, pp. 2902-2908.

Supplementary European Search Report dated Apr. 18, 2018, for corresponding European Application No. 15838781.1; consisting of 2-pages.

China National Intellectual Property Administration, Notice on the Third Office Action, dated Dec. 3, 2019, for corresponding Chinese Application No. 201580047489.0, 19 pages.

* cited by examiner

CRYOADHESIVE DEVICE FOR LEFT ATRIAL APPENDAGE OCCLUSION

CROSS-REFERENCE TO RELATED APPLICATION

This application is a Divisional of patent application Ser. No. 14/477,071, filed Sep. 4, 2014, and entitled CRYOADHESIVE DEVICE FOR LEFT ATRIAL APPENDAGE OCCLUSION, the entirety of which is incorporated herein by reference.

STATEMENT REGARDING FEDERALLY SPONSORED RESEARCH OR DEVELOPMENT n/a

FIELD OF THE INVENTION

The present invention relates to an epicardial method, system, and device for stabilizing the left atrial appendage during a left atrial appendage ligation/occlusion procedure.

BACKGROUND OF THE INVENTION

Patients with atrial fibrillation, particularly patients with non-valvular atrial fibrillation, are five times more likely of having a stroke than patients without atrial fibrillation. This increased risk is believed to original from the left atrial appendage (LAA), a muscular pouch within the pericardium and connected to the left atrium of the heart. Blood may pool within the LAA, and this pooled blood may have a tendency to form clots, which can dislodge from the LAA and form emboli. In fact, it is believed that over 90% of clots form in the LAA.

Consequently, removing or excluding (occluding) the LAA is believed to reduce the risk of stroke, especially in patients with atrial fibrillation. LAA occlusion (which may also be referred to herein as exclusion or ligation) may be accomplished by using an endocardially placed occlusion device, for example, a Transcatheter Patch (Custom Medical devices, Athens, Greece), the PLAATO™ device (ev3, Sunnyvale, Calif.), or WATCHMAN® device (Boston Scientific, Marlborough, Mass.). Alternatively, LAA occlusion may at least partially involve an epicardially placed occlusion device. There are two commonly used methods of performing LAA occlusion: one method uses endocardial and epicardial magnetized guides that stabilize the LAA by the magnetic force between the two guides through the LAA tissue. Once the LAA is stabilized, a snare is passed over the LAA and used to ligate or suture the LAA (for example, the LARIAT™ (SentreHeart, Inc. Redwood City, Calif.)). The other method involves a purely epicardial approach in which, via subxiphoid access, the LAA is identified and inserted into a clamp device (for example, the ATRICLIP® (AtriCure, Inc. West Chester, Ohio)). The clamp then remains implanted within the patient. All of these methods are meant to isolate the LAA and prevent blood clots from exiting the LAA and traveling as emboli through the bloodstream.

Of course, each of these methods has its drawbacks. For example, the magnetized guide technique may accommodate a variety of anatomies, but it requires endocardial access. The clamp technique, on the other hand, may be less versatile, but does not require the more invasive endocardial access.

It is therefore desirable to provide a method, system, and device for performing LAA occlusion that involves a purely epicardial approach and is adaptable to a variety of anatomies.

SUMMARY OF THE INVENTION

The present invention advantageously provides an epicardial device, system, and method for stabilizing the left atrial appendage (LAA) during a LAA ligation/occlusion procedure. A device for stabilizing the LAA may include a distal portion configured to be positioned within a pericardial space proximate the left atrial appendage, the distal portion including a stabilization element, the stabilization element being configured to cryoadhere to left atrial appendage tissue. The device may further comprise a proximal portion configured to be in fluid communication with a source of cryogenic fluid. Further, the stabilization element may include an expandable element, such as a balloon. The stabilization element may further include a fluid delivery element within the expandable element, and the fluid delivery element may be transitionable between a first delivery configuration and a second expanded configuration. The expandable element may define a first face and a second face when the fluid delivery element is in the second expanded configuration. The fluid delivery element may define a plurality of apertures, and all of the plurality of apertures may be directed toward one of the first face and the second face. Alternatively, the stabilization element may include a non-expandable thermally transmissive region, and the stabilization element may include a thermoelectric cooling element in thermal communication with the thermally transmissive region. The stabilization element may define an interior chamber that is in fluid communication with a source of cryogenic fluid, the thermally transmissive region being configured to be in thermal communication with the cryogenic fluid. Further, the stabilization element may have a cross-sectional shape that is one of elliptical, semicircular, or crescent shaped. The thermally transmissive region may be located on one side of the stabilization element.

A system for stabilizing a left atrial appendage of a heart may include a cryoadhesion device including a distal portion configured to be positioned within a pericardial space proximate the left atrial appendage, the distal portion including a stabilization element, and a source of cryogenic fluid in communication with the stabilization element. The distal portion may be configured to be positioned within the pericardial space through subxiphoid access. Circulation of fluid within the stabilization element may lower the temperature of the stabilization element to a temperature that is sufficient to cause cryoadhesion between the stabilization element and the left atrial appendage. The stabilization element may include a balloon defining an interior chamber and a fluid delivery element located within the balloon interior chamber and being in fluid communication with the source of cryogenic fluid, the fluid delivery element defining a plurality of apertures for the delivery of cryogenic fluid into the balloon interior chamber. The fluid delivery element may be transitionable between a first delivery configuration and a second expanded configuration, and the balloon may define a first face and a second face when the fluid delivery element is in the second expanded configuration.

An epicardial method of stabilizing a left atrial appendage of a heart may include positioning a stabilization element of a cryoadhesion device within a pericardial space proximate the left atrial appendage and cooling the stabilization element to a temperature that is sufficient to cause cryoadhesion between the stabilization element and the left atrial appendage. For example, the stabilization element may be positioned within the pericardial space through subxiphoid access. Cooling the stabilization element may include circulating cryogenic fluid within the stabilization element. The method may further include occluding the left atrial appendage with a secondary device. The stabilization element may include a balloon defining an interior chamber and a fluid delivery element located within the balloon interior chamber and being in fluid communication with the cryogenic fluid, the fluid delivery element defining a plurality of apertures for the delivery of cryogenic fluid into the balloon interior chamber.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
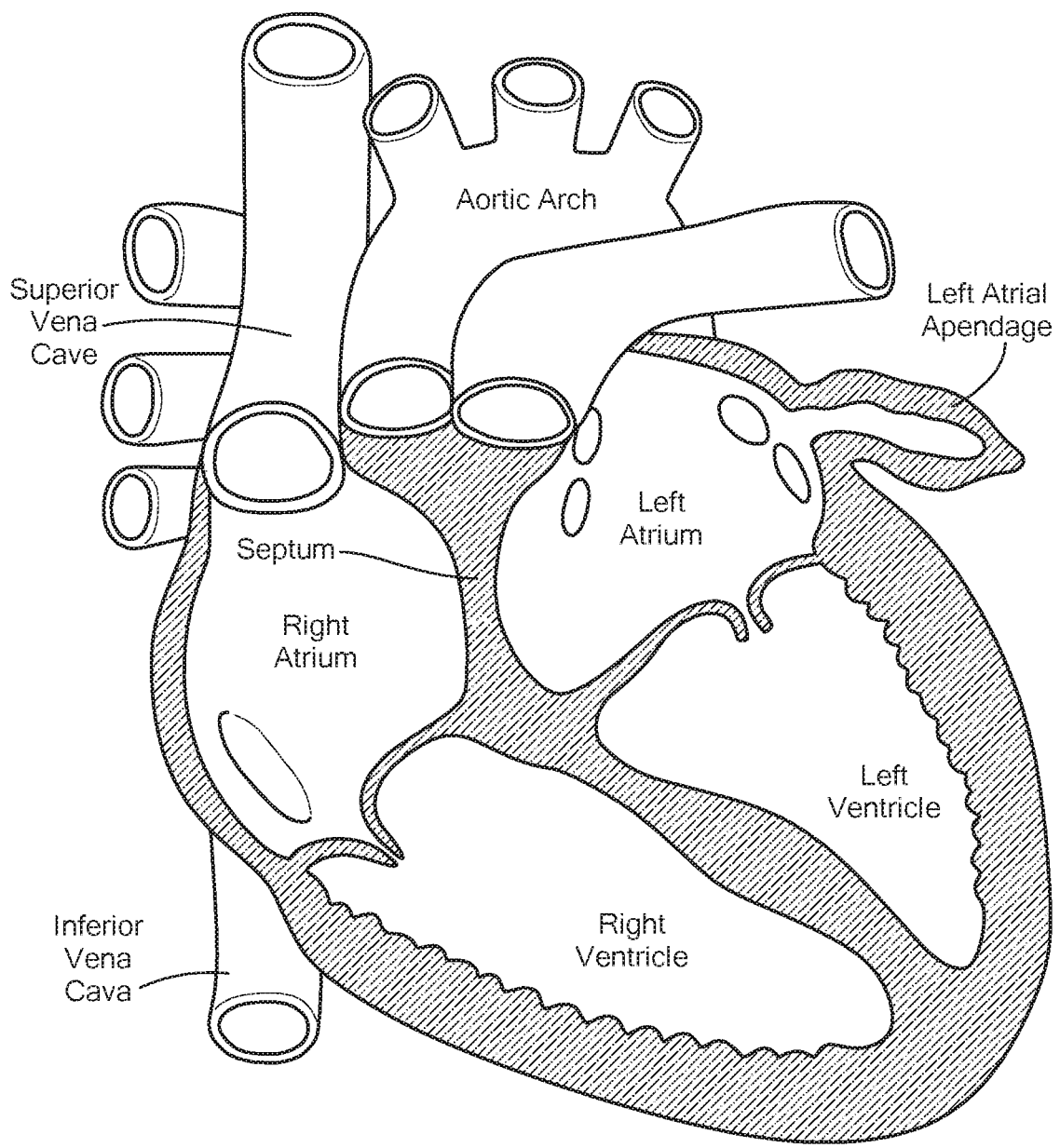
FIG. 1 shows the heart, including the left atrial appendage (LAA)

Referring now to FIG. 1, a human heart is shown. The heart includes a left atrial appendage (LAA) (also sometimes referred to as the left auricular appendix, auricular, or left auricle). The LAA is a small, muscular pouch within the pericardium that opens into the left atrium. As previously discussed, most emboli are believed to originate from the LAA, and those with atrial fibrillation are at the most risk of having a stroke. Therefore, it may be desirable to exclude, or isolate, the LAA from the patient's bloodstream to reduce the risk of emboli escaping from the LAA.

Figure 2:
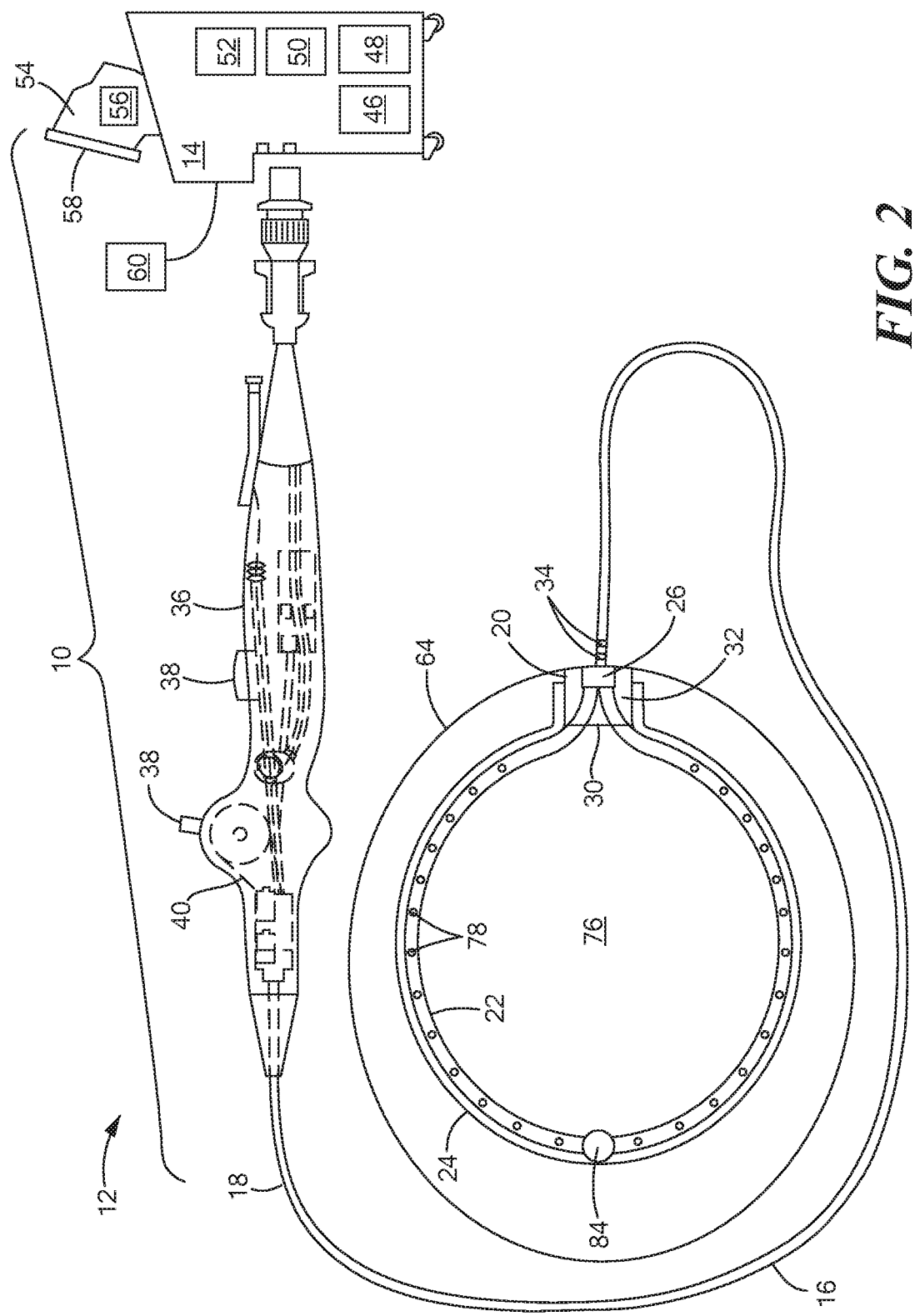
FIG. 2 shows an exemplary system that includes a first embodiment of a cryoadhesion device.

Referring now to FIG. 2, an exemplary system that includes a first embodiment of a cryoadhesion device is shown. The system 10 may generally include a cryoadhesion device 12 in fluid communication with a console 14. The device 12 may include an elongate body 16 having a proximal portion 18 and a distal portion 20, a flexible and resilient fluid delivery element 22, and an expandable element 24. The expandable element 24, for example, a cryoballoon, may be coupled to the distal portion 20 of the elongate body 16. The fluid delivery element 22 may be in fluid communication with a fluid delivery conduit 26 and may be slidably disposable or disposed within the elongate body 16, such that advancement of the fluid delivery element 22 and fluid delivery conduit 26 within the elongate body 16 may extend the fluid delivery element 22 out the distal opening 30 of the elongate body 16. Additionally or alternatively, the cryoadhesion device 12 may be passed through a guide sheath, such that advancement of the elongate body 16 of the cryoadhesion device 12 within the guide sheath may likewise advance the fluid delivery element 22 out the distal end of the guide sheath to expand the fluid delivery element 22 and retraction of the elongate body 16 of the cryoadhesion device 12 within the guide sheath may likewise retract the fluid delivery element 22 back into the guide sheath to retract the fluid delivery element 22 (as shown and described in greater detail in FIGS. 3-6). The expandable element 24 may also be in fluid communication with a fluid recovery conduit 32.

The device 12 may also include one or more electrodes 34 for monitoring an electrical signal from the LAA to obtain information such as confirmation of proper placement of the device onto LAA tissue, and for visualization with a navigation system, such as NAVX™ (St. Jude Medical, Inc., St. Paul, Minn.). The one or more electrodes may also be used to determine whether occlusion of the LAA has occurred. For example, the LAA may be stabilized or secured by the cryoadhesive device, and then a clamp or clip may be used to occlude the LAA. When the LAA is occluded, the one or more electrodes 34 may detect very few or no electrical signals from the LAA tissue. Conversely, if the one or more electrodes 34 detect a normal amount of electrical signals, the system 10 may alert the operator that the LAA is not occluded.

The device 12 may further include a handle 36 coupled to the proximal portion 18 of the elongate body 16. The handle 36 may include one or more knobs, wheels, buttons, or other actuators 38 for navigation and manipulation of the device 12. For example, the one or more actuators may be in mechanical communication with one or more steering elements, such as one or more pull wires 40, rods, or the like.

The console 14 may include a cryogenic fluid source 46 in fluid communication with the fluid delivery conduit 26, a fluid recovery reservoir 48 in fluid communication with the fluid recovery conduit 32. It will be understood that the fluid recovery reservoir 48 may be located external to the console 14; however, for simplicity, any element that is not included in the cryoadhesion device may be referred to as being a part of the console 14. The cryogenic fluid source 46 may be, for example, a nitrous oxide ($N_2O$) or carbon dioxide ($CO_2$) cartridge, and the cryogenic fluid source 46 may be located within the console 14, external to the console 14, or within the cryoadhesion device handle 36. The cryogenic fluid source 46 may be lower-volume cartridge, because cryoadhesion without ablation may be achieved with a low cryogenic fluid flow. For example, cryoadhesion may start to occur at approximately 0° C., which is warmer than temperatures required for cryoablation. Alternatively, the device 12 may be used with an existing cryoablation system, such as one having larger fluid tanks. Temperatures lower than approximately −30° C. may be used, as no detrimental effect of cryoablation to the LAA is expected before occlusion occurs. Further, the console 14 may include an energy source 50 that is in electrical communication with the one or more electrodes 34 and a vacuum source 52 that is in fluid communication with the expandable element 24 and the fluid recovery conduit 32.

The console 14 may also include one or more computers 54 having one or more processors 56 that receive data from the one or more electrodes 34 and/or one or other sensors throughout the system (for example, temperature or pressure sensors). The one or more processors 56 may also process received data using one or more algorithms to, for example, determine the temperature of the expandable element 24, whether the device 12 is cryoadhered to the LAA tissue, if the LAA has been successfully occluded, if there is a leak in the system, and/or other system and/or anatomic parameters. The console 14 may also include one or more displays 58 and user input devices 60, such as buttons, knobs, scroll wheels, keyboards, mice, touchscreens, or the like. The console 14 may communicate received and/or processed data to the operator, such as through a display screen 58 and/or one or more audible or visual alerts.

Figures 3, 4:
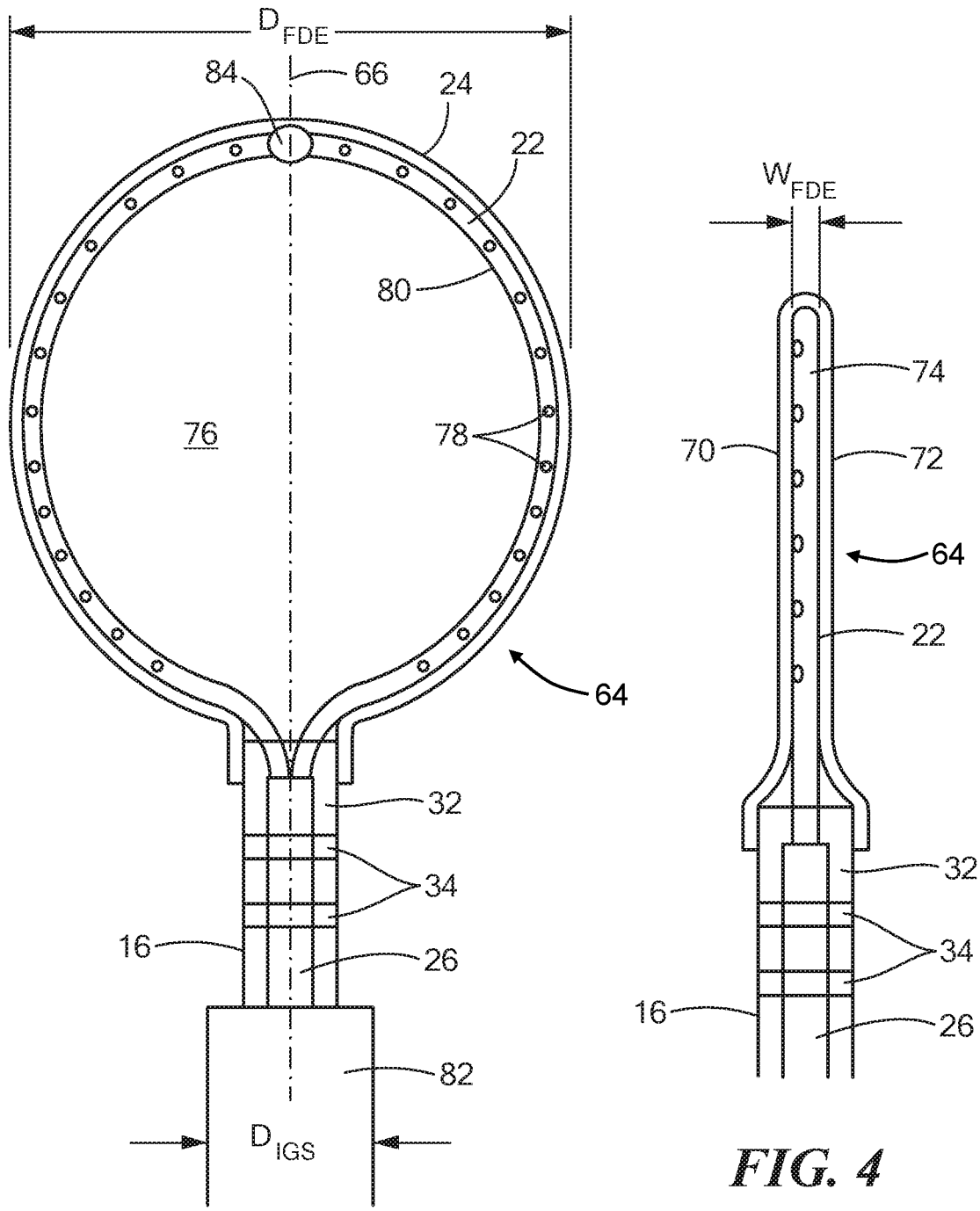
FIG. 3 shows a cryoadhesion device in an expanded configuration.
FIG. 4 shows a side view of the cryoadhesion device of FIG. 3.

Referring to FIGS. 3-6, the first embodiment of the cryoadhesion device is shown in more detail. As shown and described in FIG. 2, the device 12 may include an expandable element 24 coupled to the distal portion 20 of the elongate body 16 and a flexible and resilient fluid delivery element 22. The fluid delivery element 22 may either be that slidably received or receivable within the elongate body 16 or immovably disposed within the elongate body 16. In either configuration, the fluid delivery element 22 may be in fluid communication with the fluid delivery conduit 26. As shown in FIG. 3, the fluid delivery element 22 may have a loop shape when the fluid delivery conduit 26 is advanced within the elongate body 16, thereby extending the fluid delivery conduit 22 out of the elongate body distal opening 30. The configuration shown in FIG. 3 may be referred to as the expanded configuration.

The expandable element 24 may be, for example, a balloon that is disposed over the fluid delivery element 22, and the fluid delivery element 22 and the balloon 24 may collectively be referred to as the stabilization element 64. The stabilization element 64 may have a longitudinal axis that is coaxial with the longitudinal axis of the elongate body 16. That is, the device 12 as whole may have a single longitudinal axis 66, as shown in FIG. 3. When in the expanded configuration, the stabilization element 64 may have a flat or paddle-like shape. For example, the stabilization element 64 may define a flattened or planar first face 70, a flattened or planar second face 72, and an edge 74 between the first 70 and second 72 faces. The edge 74 may assume the curvature of the fluid delivery element 22, and the width of the edge 74 may be determined at least in part by the diameter of the fluid delivery element 22 and the thickness of the balloon 24 material. FIG. 4 shows a side view of the stabilization element 64, and it can be seen that the edge 74 may have a width that is smaller than the width of the first 70 and second 72 faces of the stabilization element 64.

Although the first 70 and second 72 faces of the stabilization element 64 may have the same thickness, in an alternative embodiment, one face may have a thickness that is greater than the other. For example, the balloon 24 may be manufactured such that the balloon material of the first face 70 is thicker than the balloon material of the second face 72. During use, the thinner second face 72 may be placed in contact with the LAA tissue. Conversely, the thicker balloon material of the first face 70 may have an insulative effect, and this warmer face may be placed in contact with non-target tissue, such as the pericardium. The warmer first face 70 may be less likely to cryoadhere to non-target tissue than the thinner second face 72, which may avoid collateral damage and patient discomfort.

When the stabilization element 64 is in the expanded configuration, cryogenic fluid may be circulated within the balloon interior chamber 76. Although circulating cryogenic fluid within the balloon interior chamber 76 may be referred to as "inflating" the balloon, it will be understood that the cryogenic fluid may be circulated at a flow rate that does not expand, or only slightly expands, the balloon beyond the width $W_{FDE}$ and the diameter $D_{FDE}$ of the fluid delivery element 22. That is, the paddle-like shape of the balloon 24 (having a flattened or planar first and second faces 70, 72) may be maintained at least in part by the expanded fluid delivery element 22 regardless of whether cryogenic fluid is circulated within the balloon chamber 76. Further, the vacuum source 52 may be activated during the LAA occlusion procedure to ensure that the stabilization element 64 is maintained in the paddle-like or flattened configuration when cryogenic fluid is circulated within the balloon chamber 76.

The fluid delivery element 22 may include a plurality of fluid delivery ports or apertures 78 for the delivery of cryogenic fluid from the fluid delivery element 22 into the balloon chamber 76. For example, the fluid delivery element 22 may include a wall 80 through which the plurality of apertures 78 extends. That is, each aperture 78 may extend through the wall 80 from an inner lumen of the fluid delivery element 22. The plurality of apertures 78 may be directed toward the interior of the chamber 76 and/or an inner surface of the balloon 24. In a non-limiting example, the plurality of apertures 78 may be directed toward the inner surface of either the first face 70 or the second face 72 of the balloon. As described in more detail below, one of the stabilization element faces 70, 72 may be cryoadhered to LAA tissue because the faces 70, 72 offer the most surface area for binding the balloon 24 and tissue. Therefore, the plurality of apertures 78 may direct the cryogenic fluid to the inner surface of one of the faces 70, 72 to maximize cooling potential of an area of the stabilization element 64 that will most efficiently stabilize the LAA. In the non-limiting embodiment shown in FIG. 4, the plurality of apertures 78 may be directed toward the inner surface of the first face 70 of the balloon 24. However, it will be understood that the plurality of apertures 78 may have any suitable configuration, such as alternating (every other aperture 78 being directed to the same one of the first 70 and second 72 faces), helically arranged, directed toward the center of the chamber 76, or the like. Each of apertures 78 may have the same or different diameters, and may be round, rectangular, slit-like, helically arranged slits, or any other suitable configuration.

Figure 5:
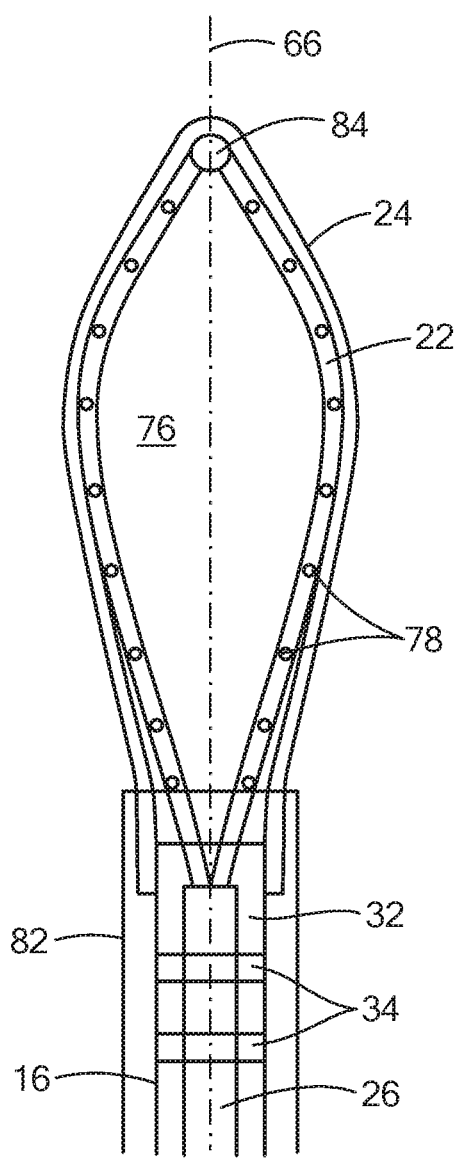
FIG. 5 shows the cryoadhesion device of FIG. 3 in a partially retracted configuration.
Figure 6:
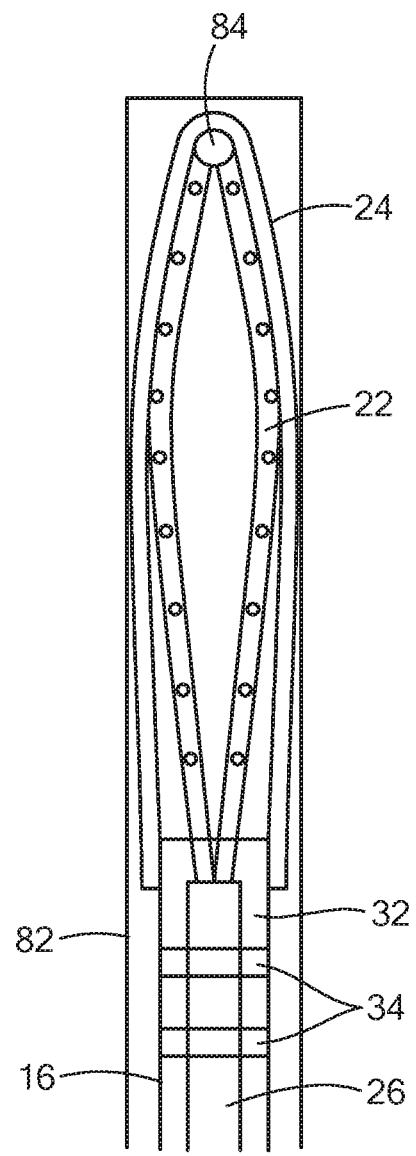
FIG. 6 shows the cryoadhesion device of FIG. 3 in a completely retracted configuration.

Referring now to FIGS. 5 and 6, the stabilization element 64 is shown being retracted within or extended out of a guide sheath 82. As described above, the fluid delivery element 22 and the fluid delivery conduit 26 may be slidably received or receivable within the elongate body 16, such that advancement or retraction of the fluid delivery conduit 26 may likewise advance or retract the fluid delivery element 22. Additionally or alternatively, the cryoadhesion device 12 may be passed through a guide sheath 82, such that advancement of the elongate body 16 of the cryoadhesion device 12 within the guide sheath 82 may likewise advance the stabilization element 64 out the distal end of the guide sheath 82 to expand the fluid delivery element 22 and retraction of the elongate body 16 of the cryoadhesion device 12 within the guide sheath 82 may likewise retract the stabilization element 64 back into the guide sheath 82 to retract the fluid delivery element 22. The fluid delivery element 22 may be composed of a material such as Nitinol or polyamide tubing that has a first neutral configuration, which may be the expanded configuration. The inner diameter of the guide sheath $D_{IGS}$ may be less than the diameter $D_{FDE}$ of the fluid delivery element 22 when the fluid delivery element 22 is in the expanded configuration. As such, when the fluid delivery element 22 is retracted within, and therefore constricted by, the guide sheath, the fluid delivery element 22 may collapse or fold into an at least substantially linear second configuration (this retracted configuration is shown in FIG. 6).

FIG. 5 shows a configuration in which the stabilization element 64 is partially retracted within the guide sheath. The flexible nature of the material from which the fluid delivery element 22 is composed will allow the fluid delivery element 22 to fold into a configuration that is narrow enough to fit within the elongate body 16 (or elongate body lumen). However, this folding may be facilitated by a pivot or bend joint 84, which may be located at the distalmost point in the fluid delivery element 22 (as shown in FIGS. 3, 5, and 6). In embodiments in which the fluid delivery element 22 includes a bend joint 84, the fluid delivery element 22 lumen may be bifurcated to include a first lumen portion extending from the fluid delivery conduit 26 to a location proximate the bend joint 84 on a first side of the fluid delivery element 22, and a second lumen portion extending from the fluid delivery conduit 26 to a location proximate the bend joint 84 on a second side of the fluid delivery element 22. When at least substantially the entire fluid delivery element 22 is extended beyond the distal opening 30 of the elongate body 16, the resilient nature of the material from which the fluid delivery element 22 is composed may cause the fluid delivery element 22 to expand back to the first neutral configuration (that is, the expanded configuration). Additionally or alternatively, the deployment and retraction of the fluid delivery element 22 may be accomplished using a push/pull wire that is in contact with the bend joint 84 at a first end and is attached to an activation mechanism in the handle 36 at a second end.

Figure 7:
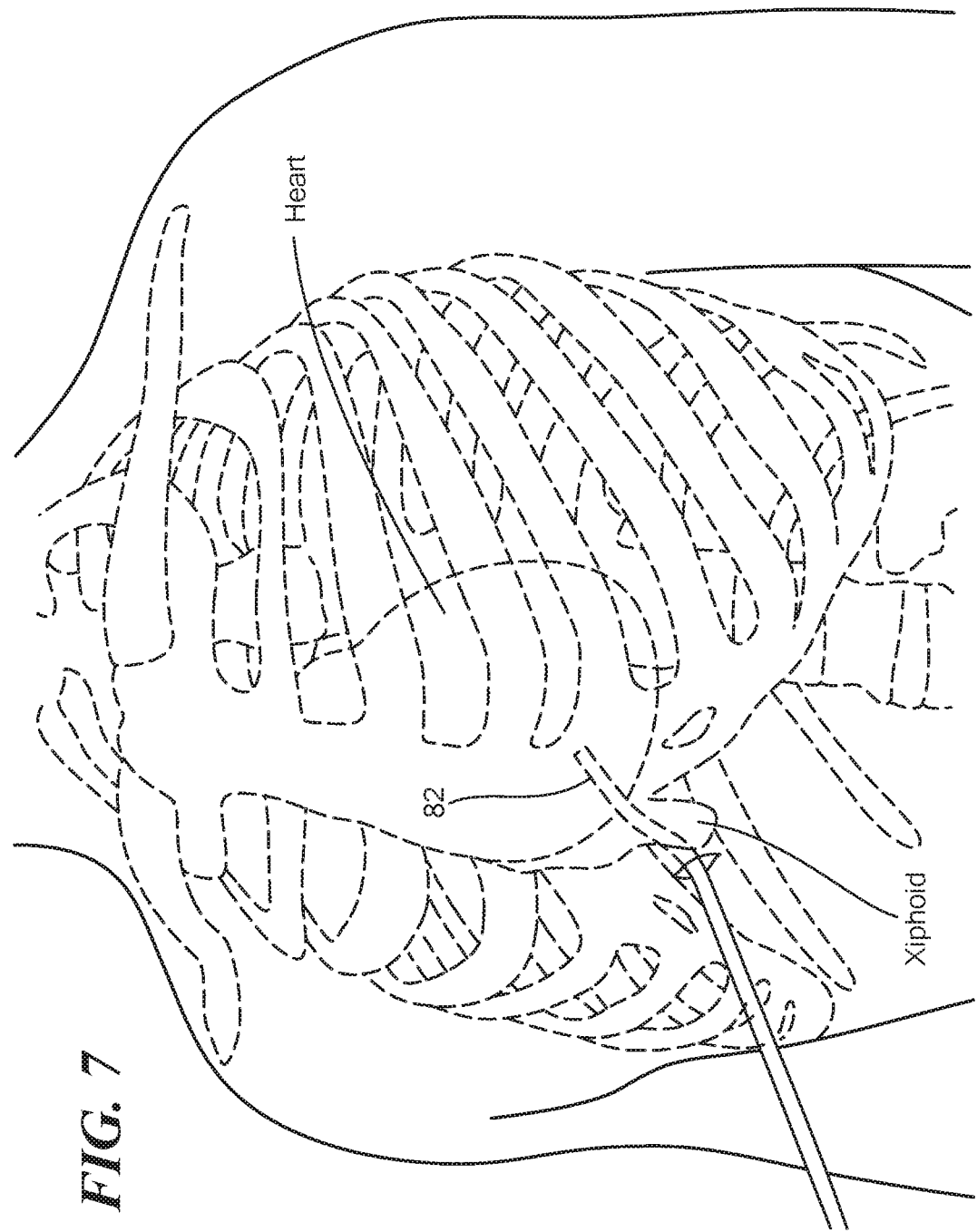
FIG. 7 shows insertion of a cryoadhesion device via subxiphoid access.

Referring now to FIGS. 7-10, insertion and placement of the cryoadhesion device 12 are shown. The device 12 may be positioned in the pericardial space (that is, between the pericardium and the heart) proximate the LAA. For example, the device 12 may be advanced through a guide sheath 82 that is inserted into the patient's body before the cryoadhesion device 12. As shown in FIG. 7, the device 12 may be inserted, within the guide sheath 82, via subxiphoid access into the pericardial space and positioned at the target treatment site proximate or in contact with the LAA, which is adjacent to the left atrium. Inserting the device into the patient's body via subxiphoid access may be less invasive and traumatic to the patient than other means of access, such as a thoracotomy. Although the device 12 is not specifically shown within the guide sheath 82 for simplicity, it will be understood that the device 12 may remain within the guide sheath 82 until the device 12 is extended beyond the guide sheath 82 at the target treatment site. During navigation through the patient's body and placement at the target treatment site, the stabilization element 64 may be in the retracted configuration. Once at the target treatment site, the fluid delivery element 22 may be advanced out the elongate body distal opening 30, which may transition the stabilization element 64 to the expanded configuration.

Figure 8:
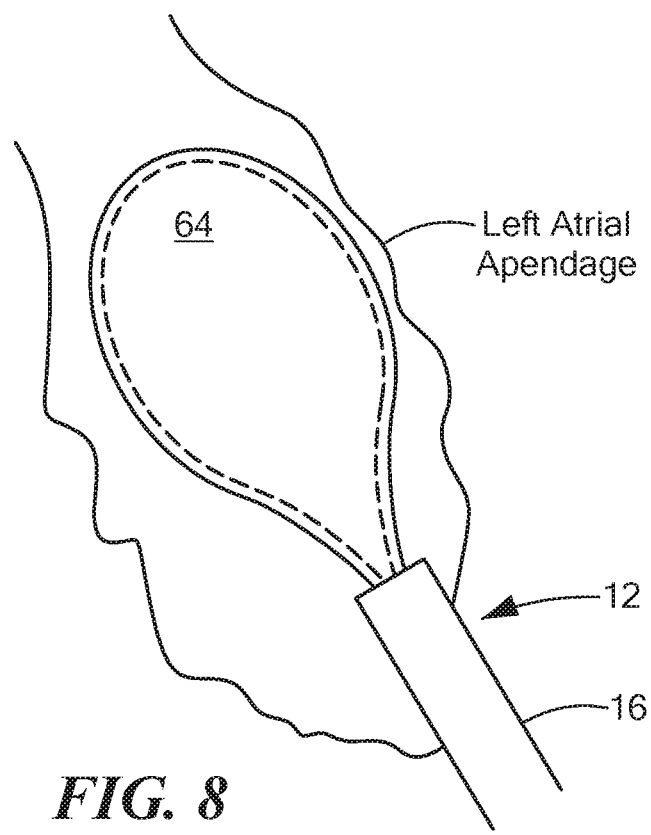
FIG. 8 shows a close-up view of placement of the first embodiment of the cryoadhesion device in contact with the LAA.
Figure 9:
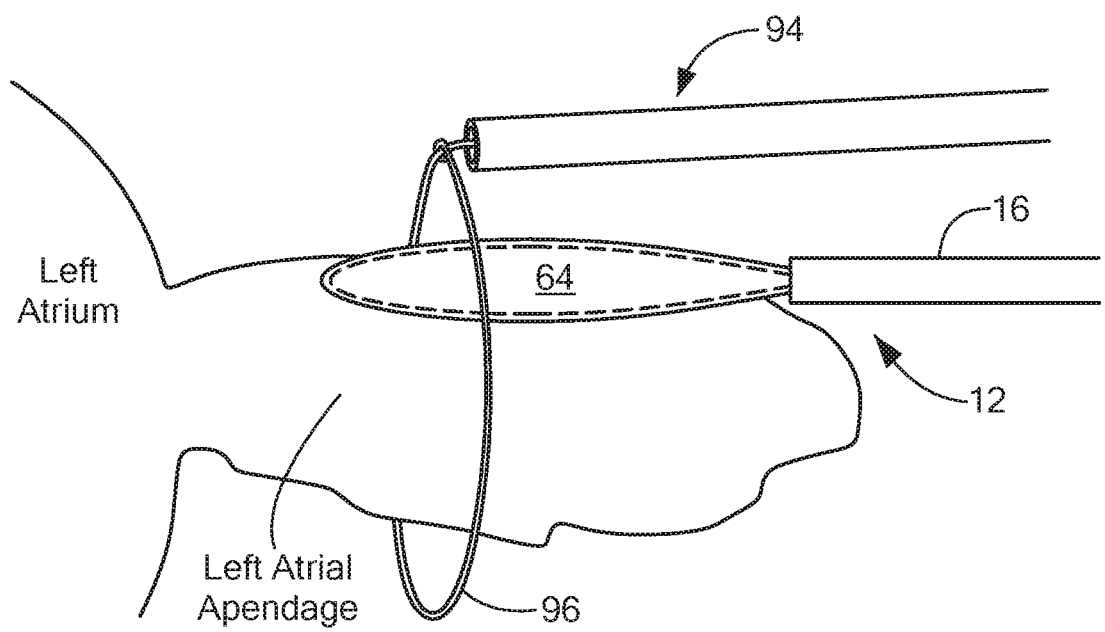
FIG. 9 shows a secondary device being positioned for ligation/occlusion of the LAA.
Figure 10:
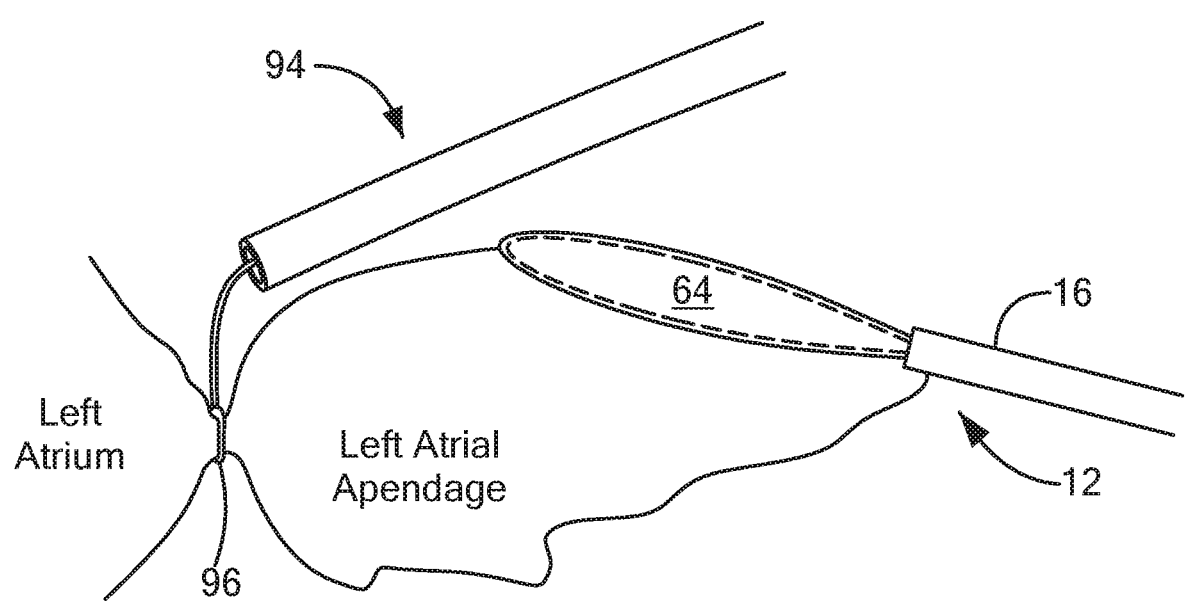
FIG. 10 shows ligation/occlusion of the LAA using the secondary device with the first embodiment of the cryoadhesion device in contact with the LAA.

Then, cryogenic fluid may be circulated within the balloon chamber 76 to reduce the temperature of the stabilization element 64 to a temperature sufficient to cryoadhere the balloon 24 to the LAA tissue (as shown in FIG. 8). Cryoadhesion between the stabilization element 64 and the LAA may be referred to as stabilization of the LAA, because the cryoadhesion allows the operator to use the device 12 to move and position the LAA for occlusion, with movement of the device 12 likewise moving the LAA. The elongate body 16 may be composed of one or more materials that give the elongate body 16 a stiffness or durometer that allows the operator to press the stabilization element 64 against the LAA tissue without the elongate body 16 collapsing. Further, unlike commonly used prior art methods, the present method does not use excessive mechanical force or suction force to stabilize the LAA, thereby reducing the likelihood of tearing or injuring the LAA tissue, which can be very thin and delicate. Further, the larger surface area of the paddle-like stabilization element 64 may distribute any applied force to a larger area of LAA tissue, including stronger trabeculated muscle of the LAA. Once the LAA is stabilized, a secondary device 94 may be used to encircle the base of the LAA, thereby occluding the LAA. As a non-limiting example, the distal loop 96 of a snare-type secondary device 94 may be fed over the elongate body 16 of the cryoadhesion device 12 (as shown from the side in FIG. 9), and then the loop 96 may be tightened around the base of, and thereby occlude, the LAA (as shown from the side in FIG. 10). Although a snare-type secondary device 94 is shown in FIG. 9, it will be understood that a clamp device or other ligation/occlusion device alternatively may be used. Further, the cryoadhesion device 12 and the secondary device 94 may be advanced to the target treatment site through the same sheath 82.

Figure 11:
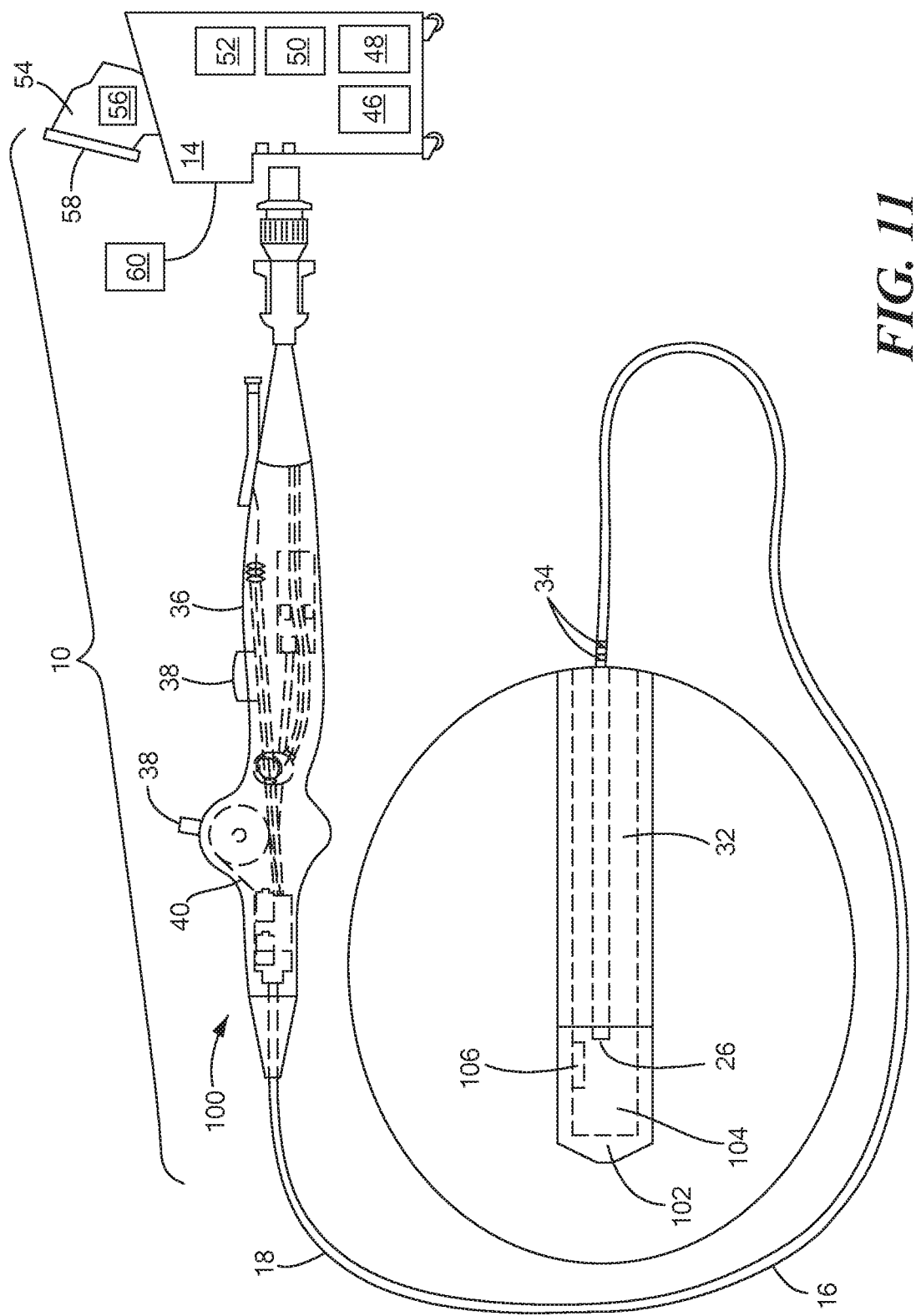
FIG. 11 shows an exemplary system that includes a second embodiment of a cryoadhesion device.
Figure 13:
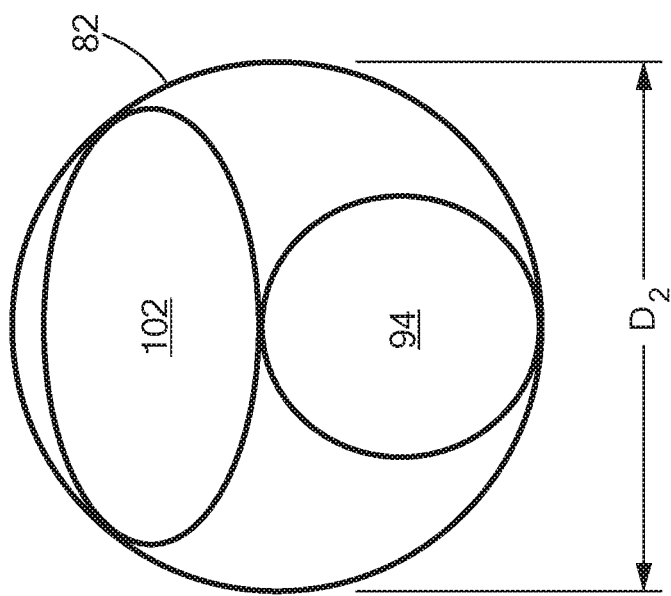
FIG. 13 shows a stylized cross-sectional view of a second configuration of the second embodiment of a cryoadhesion device and a secondary device within a guide sheath.
Figure 12:
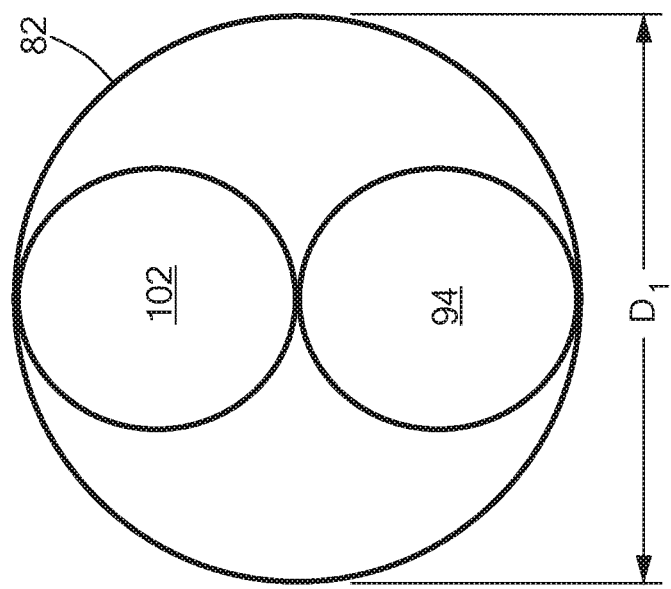
FIG. 12 shows a stylized cross-sectional view of a first configuration of the second embodiment of a cryoadhesion device and a secondary device within a guide sheath.

Referring now to FIGS. 11-18, a second embodiment of a cryoadhesion device is shown. The device second embodiment may be a focal-type device 100 with a non-expandable stabilization element 102. However, all other aspects of the system 10 not discussed herein may be as shown and described in FIG. 2. The cryoadhesion device 100 shown in FIGS. 11-18 may generally include an elongate body 16 that includes a stabilization element 102 that includes one or more thermally transmissive regions or elements at the distal portion 20. As a non-limiting example, the stabilization element may be one or more than one discrete electrodes or areas composed of material that are capable of reaching cryoadhesion temperatures (for example, approximately −30° C.), such as metal. For example, the stabilization element 102 may define an interior chamber 104 in thermal communication with the one or more thermally transmissive regions, which may be composed of a metal such as platinum, gold, copper, other such metals and/or alloys thereof, or thin polymers such as PTFE, nylon, polyurethane, polyamide, polyester, or other such compounds that can be shaped into cooling elements. Cryogenic fluid may be circulated within the interior chamber 104 and may cool the stabilization element 102 to a temperature sufficient to cryoadhere the stabilization element 102 to the LAA tissue, as described above. Additionally or alternatively, the stabilization element 102 may include one or more thermoelectric cooling elements 106, such as Peltier elements, in thermal communication with the stabilization element 102 (as shown in FIG. 11). The stabilization element 102 may entirely or partially encircle the outer circumference of the elongate body. In the non-limiting example shown in FIG. 11, the stabilization element 102 may include one thermally transmissive region that includes the distal tip of the device 100.

Referring now to FIGS. 12-16, stylized cross-sectional images of several stabilization element configurations are shown. In addition to the cryoadhesion device 100, a stylized cross-sectional image of a secondary device 94 is also shown within the sheath. These images are referred to as being stylized, because they are simplified for illustration and may not show every element of the devices 100, 94. Further, although the secondary device 94 is shown as having a circular cross section in each of FIGS. 12-15, it will be understood that the secondary device 94 may have any suitable cross-sectional shape.

Figure 15:
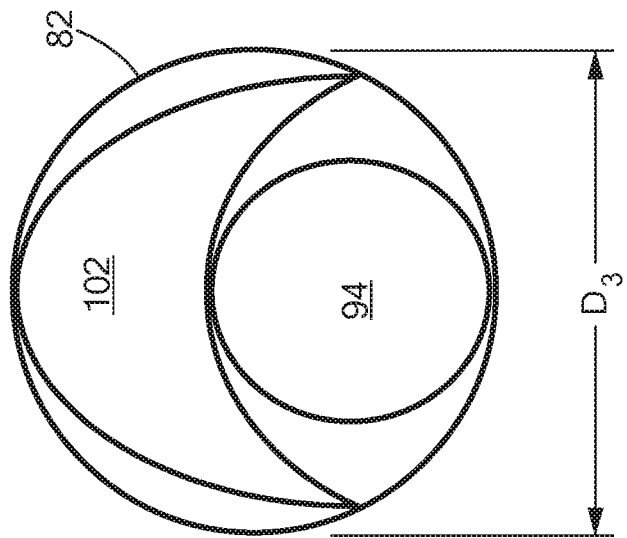
FIG. 15 shows a stylized cross-sectional view of a fourth configuration of the second embodiment of a cryoadhesion device and a secondary device within a guide sheath.
Figure 14:
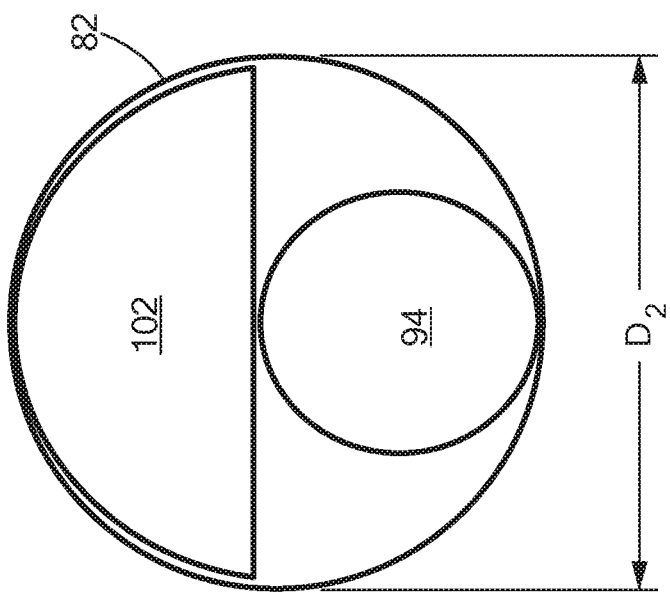
FIG. 14 shows a stylized cross-sectional view of a third configuration of the second embodiment of a cryoadhesion device and a secondary device within a guide sheath.

As non-limiting examples, the stabilization element 102 of the device 100 may have a circular cross section (FIG. 12), an elliptical cross section (FIG. 13), a semicircular cross section (FIG. 14), or a crescent-shaped cross section (FIG. 15). Although the stabilization element 102 cross sections are shown, it will be understood that the elongate body of the cryoadhesion device 100 may also have the cross-sectional shapes shown in FIGS. 12-16. A stabilization element 102 having any of these shapes may be created by A device 100 having an elliptical, semicircular, or crescent-shaped cross section may require less space within the sheath 82; therefore, a sheath 82 used to accommodate the secondary device 94 and a cryoadhesion device 100 having an elliptical, semicircular, or crescent-shaped cross section may have a smaller diameter $D_2$ than a diameter $D_1$ of a sheath 82 used to accommodate the secondary device 94 and a cryoadhesion device 100 having a circular cross section. Further, a sheath 82 used to accommodate the secondary device 94 and a cryoadhesion device 100 having a crescent-shaped cross section may have a smaller diameter $D_3$ than a sheath 82 used to accommodate the secondary device 94 and a cryoadhesion device 100 having an elliptical or semicircular cross section ($D_2$). As a non-limiting example, $D_1$ may be 20 French whereas $D_2$ may be 13-17 French. This effect may be important if the patient's anatomy cannot accept a larger-diameter sheath.

Figure 16:
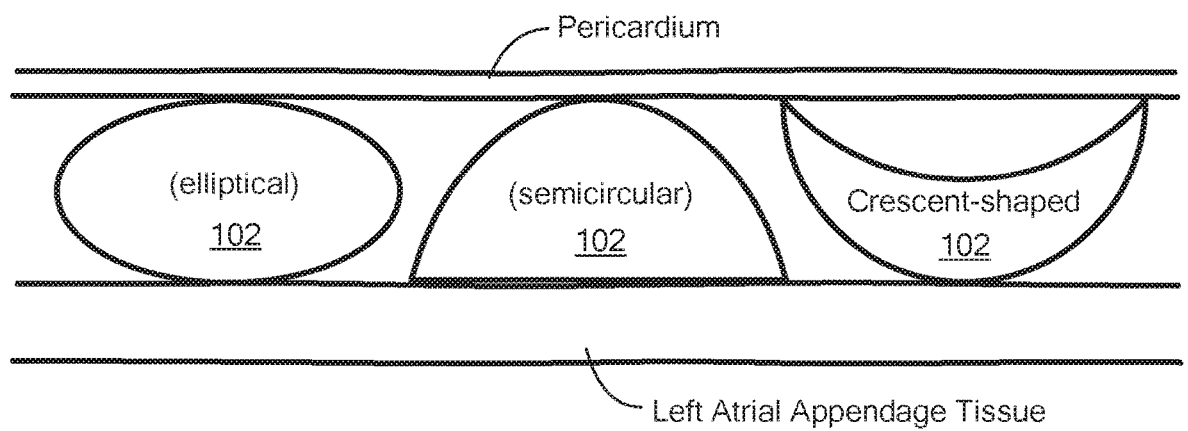
FIG. 16 shows a stylized cross-sectional view of the first, second, third, and fourth configurations of the second embodiment of a cryoadhesion device located between the LAA tissue and the pericardium.

As shown in FIG. 16, although the semicircular cross-sectional shape may be more difficult to manufacture than the circular or elliptical cross-sectional shapes, the semicircular cross-sectional shape may allow for very good contact with the LAA and less contact with the pericardium. Further, even though the crescent-shaped cross-sectional shape may be the even more difficult to manufacture than the semicircular cross-sectional shape, the crescent-shaped cross-sectional shape may allow for good contact with the LAA and very little contact with the pericardium. Less contact with the pericardium may be desirable because it reduces the risk that the stabilization element 102 may become inadvertently adhered to the pericardium. A lack of or minimal adhesion between the stabilization element 102 and the pericardium may help provide full access to the LAA by secondary devices during a ligation/occlusion procedure. Further, similar to that discussed above regarding the expandable stabilization element 64, one side of the non-expandable stabilization element 102 may be insulated or may not include any thermally transmissive regions to avoid cryoadhesion between the stabilization element 102 and non-target tissue. As a non-limiting example, the one or more thermally transmissive regions may be located around less than the entire circumference of a stabilization element 102 having a circular cross section, or on the convex side of a stabilization element 102 having a crescent-shaped cross section.

Figure 17:
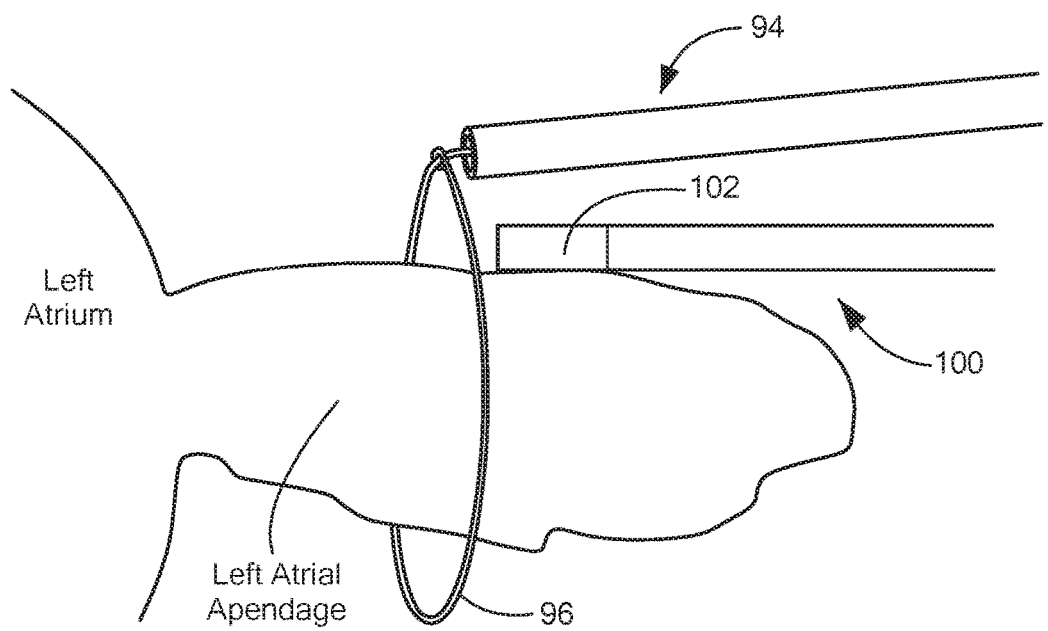
FIG. 17 shows a close-up view of placement of the second embodiment of the cryoadhesion device in contact with the LAA.
Figure 18:
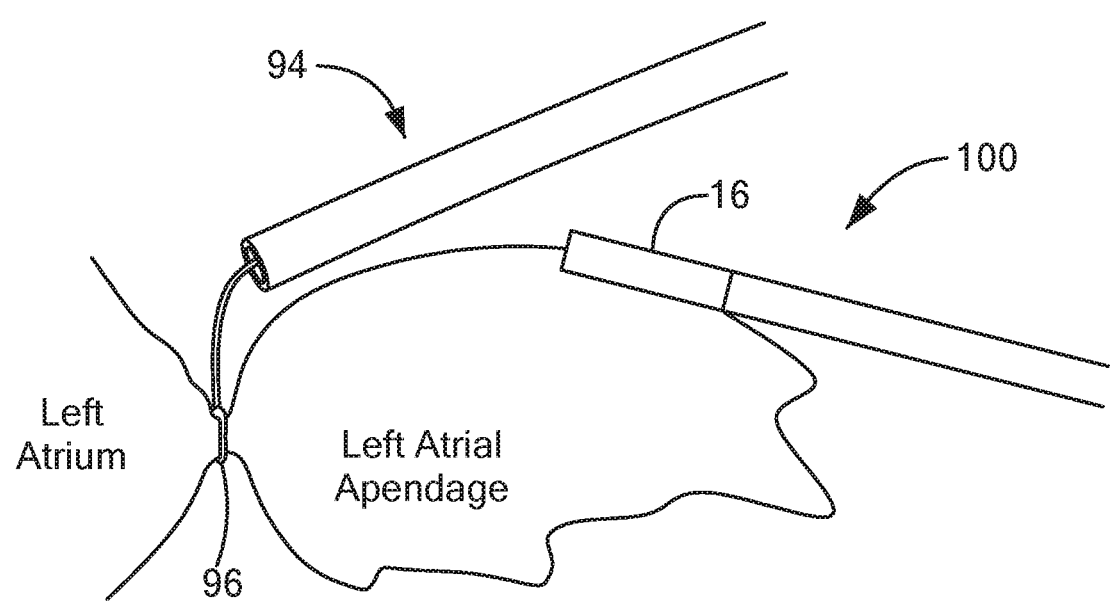
FIG. 18 shows ligation/occlusion of the LAA with a secondary device with the second embodiment of the cryoadhesion device in contact with the LAA.

Referring now to FIGS. 17 and 18, placement of the cryoadhesion device in contact with the LAA and LAA ligation/occlusion are shown. Like the first embodiment of the cryoadhesion device 12 shown in FIGS. 7-9, the second embodiment of the cryoadhesion device 100 may be positioned in the pericardial space proximate the LAA. For example, the device 100 may be advanced through a guide sheath 82 to the target treatment site via subxiphoid access. The device 100 may be delivered using a guide sheath 82 or may be navigated to the target treatment site without a guide sheath 82. Although the device 100 does not include an expandable element, cryogenic fluid may be circulated within the interior chamber 104 to reduce the temperature of the stabilization element 102 to a temperature sufficient to cryoadhere the stabilization element 102 to the LAA tissue (as shown in FIG. 17), thereby stabilizing the LAA. The elongate body 16 of the device 100 may be composed of one or more materials that give the elongate body 16 a stiffness or durometer that allows the operator to press the stabilization element 102 against the LAA tissue without the elongate body 16 collapsing. Once the LAA is stabilized, a secondary device 94 may be used to encircle the base of the LAA, thereby occluding the LAA. Although a snare-type secondary device 94 is shown in FIG. 18, it will be understood that a clamp device or other ligation/occlusion device alternatively may be used. Further, the cryoadhesion device 100 and the secondary device 94 may be advanced to the target treatment site through the same sheath 82.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An epicardial method of stabilizing a left atrial appendage of a heart, the method comprising:
positioning a stabilization element of a cryoadhesion device within a pericardial space proximate the left atrial appendage, the stabilization element including:
an expandable element, and
a fluid delivery element disposed in an interior chamber of the expandable element, the fluid delivery element having a distal end with a bend joint and a wall defining one or more apertures configured to deliver a fluid in the interior chamber, the bend joint disposed in the interior chamber of the expandable element when the fluid delivery element is in an expanded configuration, the fluid delivery element including a bifurcated lumen having a first lumen portion extending from a fluid delivery conduit to a location proximate the bend joint on a first side of the fluid delivery element and a second lumen portion extending from the fluid delivery conduit to a location proximate the bend joint on a second side of the fluid delivery element, when the fluid delivery element is in a retracted configuration, the first lumen portion and the second lumen portion bending via the bend joint to fold the fluid delivery element, cooling the stabilization element to a temperature that is sufficient to cause cryoadhesion between the stabilization element and the left atrial appendage.

2. The method of claim 1, wherein cooling the stabilization element includes circulating cryogenic fluid within the stabilization element.

3. The method of claim 2, wherein the expandable element includes:
a balloon defining the interior chamber; and
wherein the fluid delivery element located within the balloon interior chamber is in fluid communication with the cryogenic fluid and wherein the plurality of apertures deliver the cryogenic fluid into the balloon interior chamber.

4. The method of claim 1, wherein the fluid delivery element is transitionable between a first delivery configuration and a second expanded configuration.

5. The method of claim 1, wherein the stabilization element is positioned within the pericardial space through subxiphoid access.

6. The method of claim 1, further comprising:
occluding the left atrial appendage with a secondary device.

7. The method of claim 1, wherein the expandable element has:
a planar first face with a continuous surface defining a plane;
a planar second face opposite the planar first face and having a continuous surface defining a plane; and
an edge between the planar first face and the planar second face, the planar first face lying in a second plane that is parallel to the first plane and the planar second face lying in a third plane that is parallel to each of the first and second planes, the planar first face, the planar second face, and the edge defining an interior chamber.

8. The method of claim 7, further comprising occluding the left atrial appendage with a secondary device, wherein the secondary device includes a distal portion having a width that is greater than a widest portion of each of the planar first face and the planar second face such that the cryoadhesion device and stabilization element extend through the distal portion of the secondary device and the distal portion of the secondary device encircles and occludes at least a portion of the left atrial appendage when the stabilization element is cryoadhered to the left atrial appendage.

9. An epicardial method of stabilizing a left atrial appendage of a heart, the method comprising:
positioning a stabilization element of a cryoadhesion device within a pericardial space proximate the left atrial appendage, the stabilization element being configured to cryoadhere to the left atrial appendage, the stabilization element including:
an expandable element having:
a planar first face with a continuous surface defining a plane;
a planar second face opposite the planar first face and having a continuous surface defining a plane; and
an edge between the planar first face and the planar second face, the planar first face lying in a second plane that is parallel to the first plane and the planar second face lying in a third plane that is parallel to each of the first and second planes, the planar first face, the planar second face, and the edge defining an interior chamber;
a fluid delivery element disposed in the interior chamber, the fluid delivery element having a distal end with a bend joint and a wall defining a plurality of apertures configured to deliver a fluid in the interior chamber and being transitionable between a loop-shaped first configuration and a linear second configuration; and
a secondary device including a distal portion having a width that is greater than a widest portion of each of the planar first face and the planar second face such that the cryoadhesion device and stabilization element extend through the distal portion of the secondary device and the distal portion of the secondary device encircles and occludes at least a portion of the left atrial appendage when the stabilization element is cryoadhered to the left atrial appendage; and
a source of cryogenic fluid in communication with the stabilization element
cooling the stabilization element to a temperature that is sufficient to cause cryoadhesion between the stabilization element and the left atrial appendage; and
occluding the left atrial appendage with the secondary device.

10. The method of claim 9, wherein circulation of fluid within the stabilization element lowers a temperature of the stabilization element to a temperature that is sufficient to cause cryoadhesion between the stabilization element and the left atrial appendage.

11. The method of claim 10, wherein the fluid delivery element is in fluid communication with the source of cryogenic fluid.

12. The method of claim 10, wherein the stabilization element is positioned within the pericardial space through subxiphoid access.

* * * * *